United States Patent [19]

Sugimoto et al.

[11] 4,285,929
[45] * Aug. 25, 1981

[54] TYPE II INTERFERON AND AGENTS THEREOF

[75] Inventors: Kaname Sugimoto; Shokichi Yuen, both of Okayama, Japan

[73] Assignees: Shin Ashida, Hyogo; Ken Hayashibara, Okayama, both of Japan

[*] Notice: The portion of the term of this patent subsequent to Jun. 30, 1998, has been disclaimed.

[21] Appl. No.: 109,861

[22] Filed: Jan. 7, 1980

Related U.S. Application Data

[63] Continuation-in-part of Ser. No. 5,585, Jan. 22, 1979.

[30] Foreign Application Priority Data

Jan. 18, 1979 [JP] Japan .................................... 54/4544

[51] Int. Cl.³ ...................... A61K 45/02; A61K 39/00
[52] U.S. Cl. ........................................ 424/85; 435/68; 435/811
[58] Field of Search ..................... 424/85; 434/68, 811

[56] References Cited

PUBLICATIONS

Chemical Abstracts, vol. 82, p. 352, Abstract No. 1462v, Anjinsen et al., "Partial Purification of Human Interferon by Affinity Chromatography", 1974.
Chemical Abstracts, vol. 89, p. 598, Abstract No. 105634a, Berthold et al., "Purification and In Vitro Labeling of Interferon From a Human Fibroblastoid Cell Line", 1978.
Chemical Abstracts, vol. 83, p. 334, Abstract No. 25879v, Borecky et al., "Stimulation of Interferon Production in Macrophages", 1975.
Miyoshi, I., et al., Cancer, vol. 40, pp. 2999–3003, 1977.
Dianzani, F., et al., Advances in Experimental Medicine and Biology, vol. 110, pp. 119–131, 1978.
Klein, G., et al., "Sensitivity of Epstein–Barr Virus (EBV) Producer and Non–Producer Human Lymphoblastoid Cell Lines to Superinfection with E.B. Virus", Int. J. Cancer, 10, 44–57, (1972).
J.L.M., "Current and Future Sources of Interferon", Science, vol. 204, pp. 1184–1185, Jun. 15, 1979.
Epstein, L. B. "Mitogen and Antigen Induction of Interferon In Vitro and In Vivo", Texas Reports on Biology and Medicine, vol. 35, 1977, pp. 42–56.
Chemical Abstracts, vol. 81, p. 391, Abst. No. 167513d, Sano et al., "Production of Mouse Interferon . . . ", 1974.
Chemical Abstracts, vol. 79, p. 298, Abst. No. 90455k, Tovey et al., "Production of Interferon . . . ", 1973.
Chemical Abstracts, vol. 74, p. 190, Abst. No. 21415g, Khesin et al., "Cytological Study of a Peritoneal . . . ", 1971.
Chemical Abstracts, vol. 89, p. 382, Abst. No. 88763r, Zavetskii et al., "Matrix Synthesis of Mouse Interferon . . . ", 1978.
De Maeyer–Guignard, J., "Mouse Leukemia: Depression of Serum Interferon Production", Science, vol. 177, pp. 797–799, (1972).
Sata, J., "The Current Situation of the Maintenance and Duration of Tissue Culture Cell Lines in Japan", Protein, Nucleic Acid and Enzyme; vol. 20, No. 4, pp. 616–643, (1975).
Strander, H., et al., "Production of Human Lymphoblastoid Interferon", Journal of Clinical Microbiology, vol. 1, No. 1, 116–117, Jan. 1975.
Miyoshi, I., et al., "Human B Cell, T Cell and Null Cell Leukaemic Cell Liner Derived from Acute Lymphoblastic Leukaemiai", Nature, vol. 267, No. 5614, pp. 843–844, Jun. 30, 1977.
Interferon, by S. Kobayashi, Kodansha, Ltd., Tokyo, Japan, 1975.
Interferon and its Clinical Potential, by D. H. J Tyrell, William Heinemann Medical Books, Ltd., London, 1976.
Protein, Nucleic Acid and Enzyme, vol. 21, No. 4, (1976), "Interferon–Problems Concerning its Application".

Primary Examiner—Delbert R. Phillips
Assistant Examiner—Blondel Hazel
Attorney, Agent, or Firm—Browdy and Neimark

[57] ABSTRACT

The present invention relates to processes which are easily applicable for industrial production of Type II interferon and Type II interferon-containing agents.

Particularly, the present processes are based on the invention that a large amount of high-titred Type II interferon is easily obtainable by transplanting established human cells in other warm-blooded animal body or inoculating the cells in a culture medium charged in a filter-membrane-interposed diffusion chamber which is designed and fitted in or to the animal body so that the cells can grow on its nutrient body fluid, multiplying the transplanted or inoculated cells in the warm-blooded animal body or the diffusion chamber utilizing the body fluid, then exposing the multiplied cells to the action of a Type II interferon inducer in vivo or in vitro to induce Type II interferon, and purifying and separating the induced Type II interferon. The agents containing Type II interferon obtained by the method disclosed herein are effective and superior for treating and preventing Type II interferon-sensitive diseases.

10 Claims, No Drawings

TYPE II INTERFERON AND AGENTS THEREOF

CROSS REFERENCE TO RELATED APPLICATION

The present application is a continuation-in-part of U.S. application Ser. No. 5,585, filed Jan. 22, 1979.

FIELD OF THE INVENTION

The present invention relates to a process for preparing interferon, particularly Type II interferon, and to a process for preparing therapeutic and prophylactic agents thereof which are effective for Type II interferon-sensitive diseases.

BACKGROUND OF THE INVENTION

As described by Shigeyasu Kobayashi, "Interferon", published by Kodansha Co. Ltd., Tokyo, Japan (1975), D. A. J. Tyrrell, "Interferon and Its Clinical Potential", published by William Heineman Medical Books Ltd. (London) (1976), and in "Protein, Nucleic Acid and Enzyme", vol. 21, no. 4 (1976), interferon is the term designated for a proteinaceous substance which is intra- or extra-cellularly induced by exposing living cells to the action of an interferon inducer, for example virus, bacterium, protozoon, rickettsia, nucleic acid, endotoxin and polysaccharide, and which has a function to inhibit non-specifically the multiplicaton of various virus in cells. Because of its viral multiplication inhibitory function, interferon has been long considered as a promising therapeutic and prophylactic agent for viral diseases since its discovery. Recently, it has been demonstrated that interferon acts as an anti-tumor agent not only on viral tumor but also on non-viral tumor, and therefore, the realization of interferon as a medicine has been in great expectation.

It is well documented that the term interferon involves Type I and Type II interferons; the former, Type I interferon or classical interferon with a molecular weight of about $1-3 \times 10^4$, which is induced by exposing living cells to viral infections, and the latter, Type II interferon or immune interferon with a molecular weight of about $4-7 \times 10^4$, which is induced in lymphocytes on stimulation with mitogens or on response to antigens. As described by L. B. Epstein, "Texas Reports on Biology and Medicine", vol. 35, pp. 41–56 (1977), published at the University of Texas Medical Branch, Galveston, Tex., U.S.A., Type II interferon is less stable than Type I interferon under vigorous conditions; at a pH below 2 and above 10, and/or at a temperature above 56° C. Since Type II interferon, however, has a close relationship to immunoreactions, Type II interferon is expected to have much higher therapeutic and prophylactic efficacies on interferon-sensitive diseases than Type I interferon.

Due to its high species-specificity, the therapeutic and prophylactic efficacies on human diseases are not realizable with interferon which is obtained from other sources than living human cells. So far leukocytes are used in the preparation of Type II interferon. An attainment of a large amount of Type II interferon at a low cost from leukocytes is quite difficult because leukocytes must be separated and prepared from fresh blood, and do not bear long-period storages. Due to the circumstances, commercial production of Type II interferon feasible as a therapeutic and prophylactic agent for human diseases has not been realized.

SUMMARY OF THE INVENTION

The present inventors investigated processes which could be easily applied for commercial-scale production of Type II interferon and studied the possibilities of said interferon as a therapeutic and prophylactic agent. The efforts resulted in the discovery that a large amount of high-titred Type II interferon was not obtainable by transplanting and multiplying Type II interferon-producing established human cells in a nutrient culture medium in vitro, but was easily obtainable by transplanting the cells in other warm-blooded animal body or inoculating the cells in a culture medium charged in a filter-membrane-interposed diffusion chamber which is designed and fitted in or to the animal body so that the cells can grow on its nutrient body fluid, multiplying the transplanted or inoculated cells utilizing said body fluid in the warm-blooded animal body or the diffusion chamber, then exposing the multiplied cells to the action of a Type II interferon induced in vivo or in vitro to induce Type II interferon, and purifying and separating the induced Type II interferon, and that the Type II interferon obtained by the method disclosed herein was an excellent therapeutic and prophylactic agent for Type II interferon-sensitive diseases.

The process according to the present invention differs from conventional processes wherein the living cells are multiplied in vitro, and has the advantages that it requires no or much less nutrient medium supplemented with expensive serum, that the maintenance and control of the conditions during the multiplication of established human cells are easier, and that a higher-titred Type II interferon is easily obtainable. In the process according to the invention, established human cells can be easily multiplied in another warm-blooded animal body utilizing the body fluid by either transplanting the cells therein, or connecting in or to the animal body a diffusion chamber charged with a culture medium suspended with said cells, while feeding the animal in the usual way. Particularly, as compared with conventional processes wherein the cells are multiplied in vitro, the process according to the invention has additional features that the multiplication of the cells is steadier, that the multiplication rate is higher, and that the yield of induced Type II interferon per cell is much higher.

DETAILED DESCRIPTION OF PREFERRED EMBODIMENTS

Any established human cells can be used as far as they multiply readily when transplanted in other warm-blooded animal body; for example HPB-ALL cell, MOLT-3 cell, P 12/Ichikawa cell, HPB-MLT cell, P 8/Seki cell, JBL cell, HCL cell and P 10/Shibata cell, described in, "Protein, Nucleic Acid and Enzyme", vol. 23, no. 6, pp. 697–711 (1978), Namalva cell described in "Journal of Clinical Microbiology", vol. 1, pp. 116–117 (1975), and BALL-1 cell, TALL-1 cell and NALL-1 cell described by I. Miyoshi, "Nature", vol. 267, pp. 843–844 (1977). Particularly, the human lymphoblastoid cell lines are preferable. Established human cells usable in the present invention may be chosen from the above cells, although not limited to them. In steps prior to Type II interferon induction, the above cells can be used alone or in combination. To these cells, if desired, are mixed human leukocytes prepared from fresh human blood.

Any warm-blooded animal can be used in the present invention as far as established human cells can multiply therein: for example birds such as chicken and pigeon; and mammalians such as dog, cat, monkey, goat, pig, bovine, horse, rabbit, guinea pig, rat, hamster, mouse and nude mouse. Since transplantation of human cells in the above-mentioned animal bodies tends to cause undesirable immuno-reactions, animals in the most immature state, namely, egg, fetus, embryo, or new-born or infant animal, should be chosen to depress the immunoreactions as much as possible. Prior to transplantation of the cells, the animal may be irradiated with about 200–600 REM of X-ray, or $\gamma$-ray, or by injecting antiserum or an immunosuppressive agent, to depress the immunoreactions. Nude mouse, even adult, is preferable as a warm-blooded animal because it is less liable to cause undesirable immunoreactions and established human cells can be transplanted thereto and multiplied rapidly without any pre-treatment. Transplantation of multiplied human cells from one warm-blooded animal body to another warm-blooded animal body can make multiplication of the cells much steadier and the amount of Type II interferon that induced in the cells much larger; for example, established human cells are transplanted in hamsters and multiplied therein, and then the multiplied human cells are harvested and transplanted in nude mice. In this case, the multiplied cells can be transplanted further from one warm-blooded animal body to another warm-blooded animal body of the same species, genus, class or division. Established human cells can be also transplanted to any part of the animal body so far as they multiply easily therein; for example intraperitoneally, intravenously, subcutaneously or in allantoic cavity.

Instead of transplanting and multiplying established human cells in other warm-blooded animal body, any above-mentioned cells can be inoculated and multiplied in a nutrient of other warm-blooded animal body in a conventional-type diffusion chamber which is embedded, for example intraperitoneally, and devised to allow the cells to utilize said body fluid. The chambers which are usable in the invention can be of various shapes and sizes, and should be interposed with filter membranes, for example membrane filter, ultrafilter and hollow fiber, to prevent leakage of cells. Particularly, chambers with interposed filter membranes with pore sizes of about $10^{-7}$ to $10^{-5}$ m are preferable. If necessary, the diffusion chamber can be designed and placed, for example on the surface of the animal body, so that the nutrient body fluid of the animal can circulate through the chamber and the development of the established human cells inoculated in said chamber can be observed through a transparent side window made in the chamber wall. The diffusion chamber can be also designed and devised so that it can be disconnected periodically from the animal body and the cells multiply through the whole life of the animal without any unnecessary sacrifice of the animal to increase further the yield of the multiplied cells per animal. Furthermore, the process using the above-mentioned diffusion chamber has an additional feature, besides the multiplied human cells can be easily harvested because there is no direct contact of the cell with the animal cell, that various warm-blooded animals can be used without any pre-treatment to depress their immunoreactions because of their lower possibilities of causing the immunoreactions.

The process of the present invention offers the convenience that the animal to which established human cells are transplanted can be fed in the usual way and that no special treatment is required even after transplantation of cells. The period required for sufficient multiplication of the transplanted established human cells is usually about 1 to 10 weeks.

The number of the multiplied human cells was counted and found to be about $10^7$ to $10^{12}$ or more per animal. In other words, the process according to the invention is extremely advantageous for preparing Type II interferon because the number of the cells transplanted or inoculated in or to the animal body or the diffusion chamber increases about $10^2$ to $10^7$ folds or more by said process; about 10 to $10^6$ folds more than those attained by inoculating and multiplying the same cells in nutrient culture medium in vitro.

As to the induction of Type II interferon, any method can be employed as far as it induces Type II interferon in the multiplied living human cells. The cells can be exposed to the action of a Type II interferon inducer wherein they multiplied. For example, the human cells multiplied in ascites in suspension or the tumor cells that occurred subcutaneously can be exposed to the action of a Type II interferon inducer in vivo wherein they multiplied, and the induced Type II interferon is then purified and separated from the ascites or the tumor. In contrast, the multiplied human cells can be exposed after the isolation to the action of a Type II interferon inducer in vitro to induce Type II interferon. For example, the multiplied human cells harvested from ascites, or those isolated and dissociated from the massive tumors that occurred subcutaneously are suspended in a nutrient medium kept at about 20° to 40° C., to give a cell concentration of about $10^5$ to $10^8$ cells per ml, and then exposed to a Type II interferon inducer. Then, the induced Type II interferon is purified and separated. When human cells are multiplied in a diffusion chamber, the cells can be exposed to a Type II interferon inducer in said chamber in vivo, or exposed to the inducer in vitro after recovering them from said chamber.

In the production of Type II interferon, if desired, the amount of the induced Type II interferon can be augmented further by known methods such as the priming method using highly human species-specific interferon and/or the super-induction method using a metabolic inhibitor. Furthermore, the yield of the induced Type II interferon per animal can be augmented further by one or more of the following methods:

(1) a method in which the multiplied cells are first exposed to a Type II interferon inducer to induce said interferon wherein they multiplied, and then exposed after harvesting from a certain or a whole part of the animal body to a Type II interferon inducer to induce said interferon in vitro.

(2) a method in which the human cells that were already used or used repeatedly in the production of Type II inerferon are exposed to the action of a Type II interferon inducer in vivo or in vitro to induce said interferon, and (3) a method in which a diffusion chamber embedded or connected in or to the animal body is disconnected periodically to augment the number of the multiplied human cells.

As to Type II interferon inducer, usually mitogens such as phytohemagglutinin, concanavalin A, pork weed mitogen, lipopolysaccharide, polysaccharide, endotoxin and bacterium are preferable. For sensitized cells, antigen also acts as a Type II interferon inducer. The above-mentioned Type II interferon inducers are used usually in a concentration of about 0.001 μg to 10 mg per ml. In addition, the employment of one or more Type I interferon inducers, for example virus, nucleic acid and polynucleotide, in combination with a Type II interferon inducer augments further the yield of the induced Type II interferon, and also enables simultaneous induction of Type I and Type II interferons.

The induced Type II interferon can be purified and separated easily by conventional purification and separation techniques, for example salting out, dialysis, filtration, centrifugation, concentration and freeze-drying. If higher purified Type II interferon preparation is desirable, Type II interferon of the highest purity is obtainable by employing conventional techniques, for example adsorption and desorption by ion exchanger, gel filtration, affinity-chromatography, isoelectric point fractionation and electrophoresis, in combination with the above-mentioned techniques.

The activities of higher human species-specific Type I and Type II interferons were determined by the conventional plaque reduction method with human amnion cells which are described in "Protein, Nucleic Acid and Enzyme", vol. 20, no. 6, pp. 616–643 (1975), published by Kyoritsu Shuppan Co. Ltd., Tokyo, Japan.

The hemagglutination unit was assayed according to the method reported by J. E. Salk, "Journal of Immunology", vol. 49, pp. 87–98 (1944).

EXPERIMENT A below describes the production of Type II interferon according to the invention.

EXPERIMENT A

Interferon-productivity of the cells multiplied in vitro or in vivo

EXPERIMENT A-1 Multiplication in vitro

BALL-1 cells were inoculated in RPMI-1640 medium supplemented with 20% of fetal bovine serum at pH 7.2 and were cultured in suspension at 37° C. The multiplied cells were washed with serum-free RPMI-1640 medium at pH 7.2 and suspended in a fresh medium of the same composition to give a cell concentration of about $1 \times 10^6$ cells per ml.

EXPERIMENT A-2 Multiplication in vivo

New-born hamsters were pre-injected with antiserum prepared from rabbit according to the known method to depress their immunoreactions, and then were transplanted subcutaneously with BALL-1 cells. The hamsters were fed in the usual way for 3 weeks. The massive tumors that occurred subcutaneously were isolated, cut finely and dissociated in a physiological saline solution containing trypsin to collect the multiplied cells. The cells thus obtained were washed with serum-free RPMI-1640 medium at pH 7.2 and suspended in a fresh medium of the same composition to give a cell concentration of about $1 \times 10^6$ cells per ml.

EXPERIMENT A-3 Production of interferon

The suspensions of BALL-1 cells obtained in EXPERIMENT A-1 and A-2, a cell concentration of about $1 \times 10^6$ cells per ml, were exposed to phytohemagglutinin and/or Sendai virus to induce interferon. More particularly, when phytohemagglutinin was used alone, the suspensions were added with phytohemagglutinin in a proportion of about 100 μg per ml and incubated at 37° C. for 3 days to induce interferon. When Sendai virus was used alone, the suspensions were added with the virus in a proportion of about 300 hemagglutination units per ml and incubated at 37° C. for day to induce interferon. When both phytohemagglutinin and Sendai virus were used in combination, the suspensions were first added with phytohemagglutinin in a proportion of about 100 μg per ml, incubated at 37° C. for 2 days, then added with Sendai virus in a proportion of about 300 hemagglutination units per ml, and incubated at 37° C. for an additional day to induce interferon.

The interferon-containing suspensions thus obtained were centrifuged. The resulting supernatants were concentrated with an ultrafilter having a cut-off molecular weight of 6,000 and then fractionated according to the molecular weight with dextran gel. The activities of the obtained Type I interferon, molecular weight of about 25,000, and Type II interferon, molecular weight of 50,000, were determined to evaluate the interferon activities per ml suspension upon incubation. The results are shown in Table 1.

TABLE 1

| Interferon inducer | Multiplication | |
|---|---|---|
| | in vitro | in vivo |
| Phytohemagglutinin | 20 | 400 |
| | (20) | (400) |
| Sendai virus | 1,700 | 6,700 |
| | (0) | (0) |
| Phytohemagglutinin + Sendai virus | 1,740 | 24,000 |
| | (30) | (11,000) |

Note:
The determined total interferon activities upon incubation are expressed by units per ml suspension, and those of Type II interferon for each preparation are shown in parenthesis.

As obvious from the results shown in Table 1, while a small amount of interferon was induced in cells multiplied in vitro, a large amount of interferon was induced in cells multiplied in vivo. The cells multiplied in vitro as well as in vivo, produced Type I interferon when they were exposed to Sendai virus. The cells multiplied in vivo, however, gave 4 times higher activity than those multiplied in vitro. In respect to the interferon activities of the preparations induced by phytohemagglutinin and/or Sendai virus, a remarkable synergism attributed to the interferon inducers was noted in the production of Type I and Type II interferons when the cells multiplied in vivo were used. Particularly, Type II interferon induced by using phytohemagglutinin and Sendai virus in combination had an about 28 times higher activity than that induced by using phytohemagglutinin alone. No synergism was, however, observed when the cells multiplied in vitro were used.

Several embodiments illustrating the production of Type II interferon according to the present invention are shown below.

EXAMPLE A

Production of Type II interferon

Example A-1

Adult nude mice were transplanted subcutaneously with established human BALL-1 cells and were fed in the usual way for 3 weeks. The massive tumors that occurred subcutaneously, about 10 g per nude mouse, were isolated, cut finely and dissociated in a physiological saline solution containing trypsin to collect the multiplied human cells. The cells were washed with an Eagle's minimal essential medium supplemented with 5 v/v % human serum at pH 7.2, and suspended in a fresh medium of the same composition to give a cell concentration of about $5 \times 10^6$ cells per ml at 37° C. To this suspension was added a partially-purified high human species-specific interferon in a proportion of about 100 units per ml, and the mixture was incubated for about 2 hours. Phytohemagglutinin was then added to the mixture in a proportion of about 200 μg per ml. Then, the mixture was incubated at this temperature for an additional 3 days to induce Type II interferon. The incubated mixture was centrifuged at about 1,000×g and 4° C. to remove precipitates such as cell debris, and the resulting supernatant was dialyzed against a physiological saline solution bufferized at pH 7.2 with a 0.01 M phosphate buffer, for 24 hours. Then, the resultant was filtrated carefully with a filter membrane and the Type II interferon-containing filtrate was concentrated and freeze-dried into powder.

The Type II interferon activity of the powder was about 1,500,000 units per nude mouse.

Example A-2

Adult nude mice were transplanted intraperitoneally with established human BALL-1 and TALL-1 cells, and fed in the usual way for 5 weeks. The nude mice were then injected intraperitoneally with 1 mg of phytohemagglutinin, and 24 hours later they were injected with about 3,000 hemagglutination units of Newcastle disease virus whose activity was almost pre-inactivated by ultraviolet irradiation. The nude mice were sacrificed to harvest their ascites 24 hours after the injection. The ascites was centrifuged at about 1,000×g and 4° C. to remove precipitates such as cell debris. The resulting supernatant was dialyzed against a physiological saline solution bufferized at pH 7.2 with a 0.01 M phosphate buffer, for 15 hours. The resultant was then filtrated and concentrated carefully with filter membranes to obtain a concentrate containing interferon.

The total interferon activity of the concentrate was about 800,000 units per 10 nude mice, of which about 300,000 units was Type II interferon activity.

Example A-3

New-born hamsters were pre-injected with antiserum prepared from rabbit according to the known method to depress their immunoreactions and then injected subcutaneously with established human JBL cells. The hamsters were fed in the usual way for 4 weeks. The massive tumors that occurred subcutaneously, about 30 g per hamster, were isolated and treated similarly as described in Example A-1. The multiplied cells were washed with RPMI-1640 medium supplemented with 10 v/v % of fetal bovine serum at pH 7.4 and suspended in a fresh medium of the same composition to give a cell concentration of about 2×10⁷ cells per ml at 37° C. The mixture was added with a partially-purified high human species-specific Type II interferon in a proportion of about 200 units per ml and incubated at 37° C. for about one hour. The incubated mixture was then added with concanavalin A in a proportion of about 500 μg per ml, incubated for 3 days, then added with Sendai virus in a proportion of about 300 hemagglutination units per ml, and incubated for 16 hours to induce interferon. The mixture was purified and concentrated carefully with filter membranes similarly as described in Example A-2 to obtain an interferon-containing solution.

The total interferon activity of the solution was about 17,000,000 units per hamster, of which about 6,000,000 units was Type II interferon activity.

Example A-4

New-born rats were transplanted intravenously with established human Namalva cells and then fed in the usual way for 4 weeks. The massive tumors that occurred subcutaneously, about 50 g per rat, were isolated, cut finely and dissociated similarly as described in Example A-1. The multiplied human cells were treated similarly as described in Example A-1, except that Maruyama vaccin was added in a proportion of about 1 μg per ml to induce Type II interferon instead of phytohemagglutinin. The induced Type II interferon was purified and the resulting solution containing Type II interferon was freeze-dried into powder similarly as described in Example A-1.

The Type II interferon activity of the powder was about 8,000,000 units per rat.

Example A-5

At first, adult mice were irradiated with about 400 REM of X-ray to depress their immunoreactions, then transplanted subcutaneously with established human TALL-1 cells and fed in the usual way for 3 weeks. After isolating and cutting finely the massive tumors that occurred subcutaneously, about 10 g per mouse, the tumor cells were dissociated similarly as described in Example A-1. The cells were treated similarly as described in Example A-3 to induce interferon. The induced interferon was purified and concentrated similarly as described in Example A-2 to obtain a concentrate containing interferon.

The total interferon activity of the concentrate was about 9,000,000 units per mouse, of which about 3,000,000 units was Type II interferon activity.

Example A-6

Hamsters were first transplanted subcutaneously with established human MOLT-3 cells similarly as described in Example A-3 and fed in the usual way for 3 weeks to multiply the cells. Ten-day-old nude mice were then transplanted intraperitoneally with the multiplied cells and fed in the usual way for an additional 5 weeks. The nude mice were anesthetized to harvest their ascites. The obtained ascites was centrifuged to harvest the multiplied cells. The cells were washed and treated similarly as described in Example A-1 to induce Type II interferon. The induced Type II interferon was then purified and concentrated similarly as described in Example A-2 into a concentrate containing Type II interferon.

The Type II interferon activity of the concentrate was about 500,000 units per nude mouse.

Example A-7

Using plastic cylindrical diffusion chamber with interposed membrane filters, pore sizes of 0.5μ and capasities of about 10 ml, established human JBL cells were suspended in physiological saline solution. The chambers were embedded intraperitoneally in adult rats. The rats were fed in the usual way for 4 weeks and the chambers were removed. The concentration of the multiplied human cells in the chambers was about 5×10⁹ cells per ml which was about 1,000 times or more higher than that attained in vitro in a nutrient medium using a $CO_2$ incubator. The suspension of the obtained cells was added with MOLT-3 cells prepared in Example A-6 to give a concentration of about 20 v/v % and the mixture was treated similarly as described in Example A-1 to induce Type II interferon. The induced Type II interferon was purified and concentrated into a concentrate containing Type II interferon which was then freeze-dried into powder.

The Type II interferon activity of the powder was about 4,000,000 units per rat.

Example A-8

Established human NALL-1 cells were transplanted in the allantoic cavities of embryonated eggs which had been pre-incubated at 37° C. for 5 days, and the eggs were incubated at this temperature for an additional 7 days. The eggs were opened and the multiplied human cells were harvested. The suspension of the cells was added in equivolume with TALL-1 cells prepared in Example A-5 and treated similarly as described in Example A-1 to induce Type II interferon. The induced Type II interferon was purified and concentrated similarly as described in Example A-2 to obtain a concentrate containing Type II interferon.

The Type II interferon activity of the concentrate was about 300,000 units per 10 embryonated eggs.

Example A-9

A powder prepared by the method described in Example A-1 was further purified carefully in a pH range of 4 to 9 with conventional methods such as adsorption and desorption by ion exchanger, fractionation according to the molecular weight with gel filtration, concentration and careful filtration, as described in Bodo's report, "Symposium on Preparation, Standardization and Clinical Use of Interferon. 11th International Immunobiological Symposium. 8 & 9 June (1977), Zagreb, Yugoslavia". A highly purified interferon preparation with a specific activity of $2 \times 10^6$ units per mg protein was obtained and the total recovery was about 40%.

The results of EXPERIMENT B demonstrate that the Type II interferon obtained according to the methods described in the above Examples can be used solely, in combination with Type I interferon, or in mixtures with one or more other substances, as an effective therapeutic and/or prophylactic agent that can be used as injection or medicine for external or internal administration, for Type II interferon-sensitive diseases.

EXPERIMENT B

Therapeutic and prophylactic effects of Type II interferon on interferon-sensitive diseases

EXPERIMENT B-1

Therapy of viral diseases with Type II interferon (inhibitory effect on viral multiplication in vitro)

To mono-layers of human embryonic lung cells formed by primary culture in Petri dishes, 6 cm in diameter, were added 0.1, 1.0, or 10.0 units of the Type II interferon prepared by the method in Example A-9 and the obtained mixtures were incubated in a 5 v/v % $CO_2$ incubator at 37° C. for 20 hours. To the cells were added varicella zoster virus or human cytomegalo virus in the amount that forms 100 plaques in the absence of Type II interferon. The admixtures were incubated and the numbers of the formed plaques were counted.

The inhibitory effect of Type II interferon on the viral multiplication was determined using the following equation.

$$\text{Reduction of the number of plaques (\%)} = \frac{A - B}{A} \times 100$$

wherein A is the number of the plaques formed in the absence of Type II interferon, and B the number of the plaques formed in the presence of Type II interferon. The results are shown in Table 2.

TABLE 2

| Type II interferon | Varicella zoster virus | Human cytomegale virus |
|---|---|---|
| 0 unit | 0% | 0% |
| 0.1 unit | 8% | 6% |
| 1.0 unit | 49% | 54% |
| 10.0 units | 88% | 83% |

As obvious from the results in Table 2, the Type II interferon used in the present invention inhibited effectively the multiplication of the viral disease-causative virus. In the test, addition of the Type II interferon caused no abnormality in human cells.

EXPERIMENT B-2

Therapy of non-viral diseases with Type II interferon (1) Inhibition of the tumor cell multiplication in vitro The Type II interferon prepared by the method in Example A-9 was added to RPMI-1640 medium supplemented with 15 v/v % fetal bovine serum to give the final concentration of 5, 50, or 500 units per ml. To the mixtures were transplanted various tumor cells to give the concentration of $5 \times 10^5$ cells per ml. The mixtures were then incubated in a 5 v/v % $CO_2$ incubator at 37° C. for 5 days and the numbers of the cells per ml medium were counted. Control experiments were carried out similarly as in the above experiments, except that a Type II interferon which was pre-inactivated by heating at 100° C. for 30 minutes was used.

The inhibitory effect of Type II interferon on tumor cell multiplication was determined by the following equation.

$$\text{Inhibition of the tumor cell multiplication (\%)} = \frac{(A - 5 \times 10^5) - (B - 5 \times 10^5)}{(A - 5 \times 10^5)} \times 100$$

wherein A is the number of the cells of the control, and B the number of the cells of the experiment with Type II interferon. The results are shown in Table 3.

As obvious from the results shown in Table 3, the Type II interferon which was used in the present invention inhibited effectively the multiplication of the tumor cells such as BALL-1 cell, TALL-1 cell, NALL-1 cell and JBL cell, and was effective over an active concentration range of 5 to 500 units per ml.

TABLE 3

| Type II interferon concentration | Human tumor cell | | | |
|---|---|---|---|---|
| (units per ml) | BALL-1 | TALL-1 | NALL-1 | JBL |
| 5 | +17% | +13% | +19% | +18% |
| 50 | +55% | +59% | +61% | +50% |
| 500 | +84% | +80% | +86% | +89% |

(2) Inhibition of the tumor cell multiplication in vivo

The test was carried out with 8 nude mice, about 2-month-old.

TALL-1 cells were transplanted subcutaneously in all 8 nude mice in the proportion of $7.5 \times 10^6$ cells per nude mouse. From the second day after the transplantation, 4 nude mice were given 3 intraperitoneal injections of 1,000 units of Type II interferon prepared by the method in Example A-6 a week, 20 injections in total. Forty eight days later, the nude mice were sacrificed and the wet weights of the occurred massive tumors were weighed. Control experiment was carried out with the remaining 4 nude mice similarly as in the above experiment, except that they did not receive Type II interferon.

The results are shown in Table 4.

TABLE 4

| Experiment No. | Control | Type II interferon-treated nude mouse |
|---|---|---|
| 1 | 5.6 g | 1.3 g |
| 2 | 4.5 g | 0.8 g |
| 3 | 9.0 g | 0 g |

TABLE 4-continued

| Experiment No. | Control | Type II interferon-treated nude mouse |
|---|---|---|
| 4 | 6.3 g | 0 g |
| Average weight | 6.3 g | 0.5 g |

(3) Inhibition of the tumor cell multiplication in vivo

The test was carried out with 8 nude mice, about 2-month-old.

Tumor JBL cells were transplanted subcutaneously in all 8 nude mice in the proportion of $1 \times 10^7$ cells per nude mouse. From the second week after the transplantation, 4 nude mice were given 2 intraperitoneal injections of 1,000 units of Type II interferon prepared by the method in Example A-2 a week, 8 injections in total. Forty two days later, the nude mice were sacrificed and the wet weights of the occurred massive tumors were weighed. Control experiment was carried out with the remaining 4 nude mice similarly as in the above experiment, except that they did not receive Type II interferon. The results are shown in Table 5.

TABLE 5

| Experiment No. | Control | Type II interferon-treated nude mouse |
|---|---|---|
| 1 | 4.7 g | 0.5 g |
| 2 | 6.2 g | 0.5 g |
| 3 | 15.3 g | 0.5 g |
| 4 | 16.9 g | 0.8 g |
| Average weight | 10.8 g | 0.6 g |

As obvious from the results in Table 4 and 5, the Type II interferon injection inhibited tumor formation, and also inhibited extremely development even when it occurred; the wet weights of the occurred massive tumors of the Type II interferon-treated nude mice were much less than those of the controls. In addition, the Type II interferon-treated nude mice showed better appetites and were more active than the controls.

EXPERIMENT C

Acute toxicity

The acute toxicity test of the Type II interferon preparation prepared by the method in Example A-9 was carried out with 20-day-old mice, and demonstrated that the toxicity of said Type II interferon preparation was extremely low: $LD_{50}$ value, 20,000,000 units or more per kg in the case of intraperitoneal injection.

As obvious from the above experiments, Type II interferon-sensitive diseases referred in the invention can be those which can be treated and prevented with the interferon prepared in accordance with the present invention; for example viral diseases such as epidemic keratoconjunctivitis, herpetic keratitis, influenza, rubella and serum hepatitis, and non-viral diseases such as certain types of cancer.

The therapeutic and prophylactic agents containing Type II interferon that can be used for said Type II interferon-sensitive diseases are preparable in various forms and phases according to the use, for example liquid preparations for nebula, eye wash, nose drop, gargle and injection, paste preparation such as ointment, and solid preparations in powder, granule and tablet. The agents are sufficiently effective when Type II interferon contents are 1 to 10,000,000 units per g, and if desired, can be used in combination or in mixture with one or more other substances, for example therapeutic agent, vehicle, filler and stabilizer.

Particularly, since interferon, when injected intravenously, is readily eliminated from blood within about 10 minutes and excreted from the system, instillation administration of interferon, for example by incorporating interferon into instillation sugar supplement solution, provides means to prolong the administration time to render full and effective utilization of the instilled interferon and to improve further the therapeutic and prophylactic actions of interferon on interferon-sensitive diseases.

Several embodiments for Type II interferon-containing preparations according to the present invention are described below.

EXAMPLE B

Preparations containing Type II interferon

Example B-1. Liquid preparation

A liquid preparation was prepared by dissolving the Type II interferon-containing powder prepared by the method in Example A-1 in physiological saline solution in a proportion of about 500 units per ml.

The preparation is suitable as nebula, eye wash, nose drop, and gargle in treating and preventing viral diseases; particularly, epidemic keratoconjunctivitis and influenza.

Example B-2. Injection

An injection was prepared by mixing the Type II interferon prepared by the method in Example A-9 in physiological saline solution in a proportion of about 100,000 units per ml.

The injection is suitable for treating and preventing all Type II interferon-sensitive diseases including viral and certain tumorous diseases.

Example B-3. Sugar supplemental injection solution

A sugar supplemental injection solution for intravenous instillation was prepared by mixing 1,000,000 units of an interferon preparation, containing Type I and Type II interferons which were both prepared by the method described in Example A-5, and 100 mg of cyclophosphamide in 500 ml of a 10 w/v % aqueous maltose solution.

The sugar supplemental injection solution is suitable as a continuous-intravenous-infusion solution for treating and preventing certain tumorous diseases.

Example B-4. Injection

An injection was prepared by dissolving 500,000 units of interferon preparation containing Type I and Type II interferons prepared by the method in Example A-2 and 2 mg of mitomycin C in 100 ml of a 10 w/v % aqueous maltose solution.

The injection is suitable for treating and preventing tumorous diseases.

Example B-5. Ointment

An ointment was prepared according to the conventional method by mixing the powder prepared by the method of Example A-4, liquid paraffin and vaseline to give a Type II interferon activity of 10,000 units per g.

The ointment is suitable for treating viral skin diseases.

Example B-6. Tablet

Tablets were prepared according to the conventional method by tabletting a mixture of the Type II interferon-containing powder prepared by the method in Example A-7, starch and maltose to give a Type II interferon activity of about 1,000 units per tablet (about 100 mg).

The tablets are suitable for treating and preventing viral diseases that occurred in the digestive system.

Example B-7. Liquid preparation

A liquid preparation for oral administration was prepared by dissolving 5 mg of methotrexate and the concentrate having a Type II interferon activity of 200,000 units prepared by the method in Example A-8 in 10 ml of a 10 w/v % aqueous maltose solution.

The preparation is suitable for treating and preventing certain tumorous diseases.

What we claim is:

1. A process for preparing human-specific Type II interferon, comprising:
    transplanting Type II interferon-producing established human cells into a non-human warm-blooded animal body;
    multiplying the transplanted cells in a warm-blooded animal body;
    exposing the multiplied human cells to the action of Type II interferon inducer in vivo or in vitro to induce Type II interferon; and
    purifying and separating the induced Type II interferon.

2. A process for preparing human-specific Type II interferon, comprising:
    inoculating Type II interferon-producing established human cells onto a nutrient medium in a diffusion chamber having pores of about $10^{-7}$ to $10^{-5}$ m in diameter;
    placing the diffusion chamber in or on the body of a non-human warm-blooded animal such that the nutrient body fluids of the animal have access to the chamber;
    multiplying the inoculated cells while allowing the animal to supply the cells with its nutrient body fluid;
    exposing the multiplied human cells to the action of a Type II interferon inducer to induce Type II interferon;
and
    purifying and separating the induced Type II interferon.

3. A process according to claim 1 or claim 2, in which the Type II interferon-producing established human cells are human lymphoblastoid cell lines.

4. A process according to claim 1 or claim 2, in which the Type II interferon-producing established human cells are HPB-ALL cells, MOLT-3 cells, P 12/Ichikawa cells, HPB-MLT cells, P 8/Seki cells, HCL cells, P 10/Shibata cells, Namalva cells, BALL-1 cells, TALL-1 cells, NALL-1 cells or JBL cells.

5. A process according to claim 1 or claim 2, in which more than one line of established human cells are used.

6. A process according to claim 1 or claim 2, in which the non-human warm-blooded animal is mammalian.

7. A process according to claim 6, in which the mammalian is a dog, cat, monkey, pig, bovine, horse, goat, rabbit, guinea pig, rat, hamster, mouse or nude mouse.

8. A process according to claim 1 or claim 2, wherein said exposing step comprises exposing the multiplied human cells to both Type I interferon and Type II interferon inducers in combination.

9. A process according to claim 1 or claim 2, in which the multiplied human cell suspension is exposed to the action of an interferon inducer at an interferon inducer concentration of about 0.001 μg to 10 mg per ml.

10. A process according to claim 1 or claim 2, in which the multiplied human cells are exposed to the action of an interferon inducer at a temperature of about 20° to 40° C.

* * * * *